United States Patent [19]

Knöchel

[11] Patent Number: 4,546,311

[45] Date of Patent: Oct. 8, 1985

[54] ARRANGEMENT FOR MEASURING MOISTURE CONTENT

[75] Inventor: Reinhard Knöchel, Kölln-Reisiek, Fed. Rep. of Germany

[73] Assignee: U.S. Philips Corporation, New York, N.Y.

[21] Appl. No.: 450,314

[22] Filed: Dec. 16, 1982

[30] Foreign Application Priority Data

Dec. 18, 1981 [DE] Fed. Rep. of Germany ....... 3150202

[51] Int. Cl.⁴ ............................................ G01R 27/04
[52] U.S. Cl. ............................................... 324/58.5 R
[58] Field of Search ................... 324/58.5 R, 58.5 A, 324/58.5 B, 58 R

[56] References Cited

U.S. PATENT DOCUMENTS 2,798,197 7/1957 Thurston ........................ 324/58.5 B
4,052,666 10/1977 Fletcher ......................... 324/58.5 B

OTHER PUBLICATIONS

Berliner: "Phase Sensitive UHF Moisture Gauge"–Ind. Lab. (USA)–vol. 37, No. 10, Oct. 1971 (translated Zavodskaya Laboratoriya–Oct. 71)–USCL.

Kraszewski: "An Improved MW Method of Moisture Content Measurement and Control", IEEE Transaction on Industrial Electronics & Control Instr.–Nov. 76.

Primary Examiner—Stanley T. Krawczewicz
Assistant Examiner—Jose M. Solis
Attorney, Agent, or Firm—Robert J. Kraus

[57] ABSTRACT

An arrangement for measuring the moisture content of an aqueous substance by using microwaves produced by a transmitting arrangement formed by a signal source and a transmit aerial connected thereto. A portion of the aqueous substance is disposed in the field of radiation of the transmit aerial, and a receive aerial for receiving the transmitted wave is immersed in the substance. An evaluation arrangement is connected to the receive aerial for measuring a phase change of the wave in the substance. The phase change represents the moisture content of the substance.

8 Claims, 9 Drawing Figures

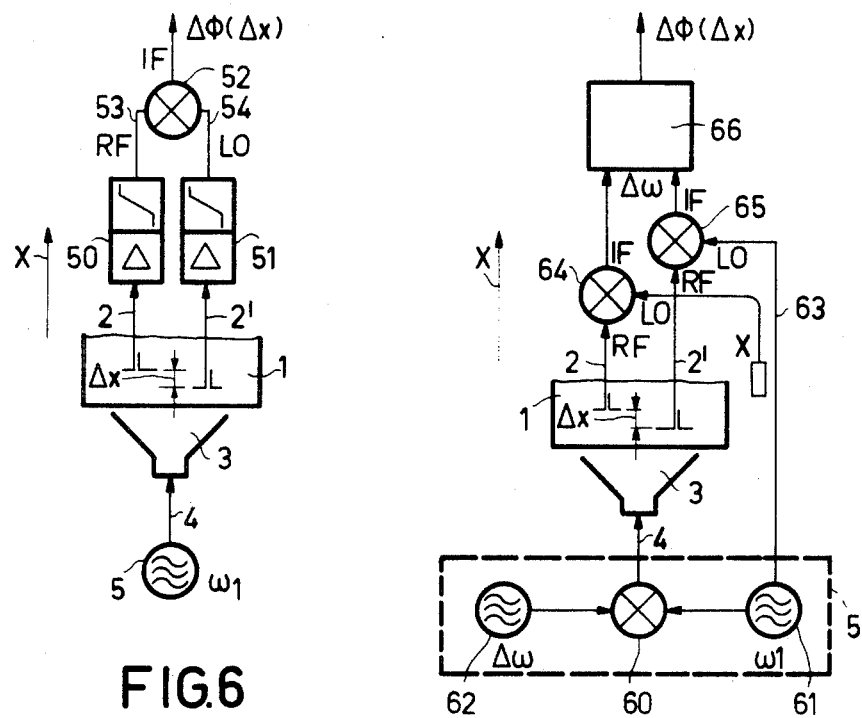
FIG.6
FIG.7
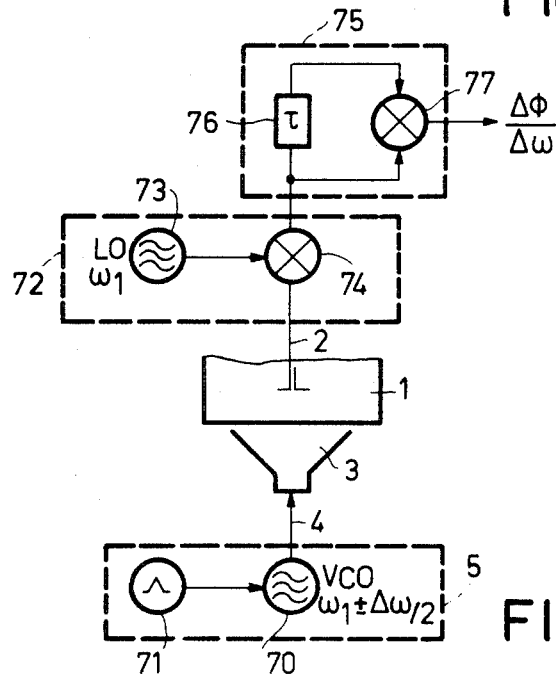
FIG.8

ARRANGEMENT FOR MEASURING MOISTURE CONTENT

BACKGROUND OF THE INVENTION

The invention relates to an arrangement for measuring the moisture content of an aqueous substance by using microwaves produced by a transmitting arrangement formed by a signal source and a transmit aerial connected thereto. The aqueous substance is disposed in the field of radiation of the transmit aerial a receive aerial and receives the wave transmitted through the substance. An evaluation arrangement is connected to the receive aerial.

Several arrangements for measuring the moisture content of an aqueous substance by means of microwaves are known. The "Proceedings of the Microwave Power Symposium", Toronto, 9-12 June 1980, pages 193-195 discloses an arrangement in which a coaxial aerial ends in a tube in which the substance to be measured is present. The coaxial aerial is connected to a measuring arrangement which determines the reflection factor of the coaxial aerial, which depends on the permittivity and consequently on the water content of the substance present in the tube.

This measuring arrangement has the disadvantage that a very accurate and consequently costly determination of the permittivity at the end of the coaxial aerial is required. In addition, only that portion of the substance to be measured which, in the tube, is in the immediate vicinity of the coaxial aerial influences the measured reflection factor. Consequently, the measuring arrangement is not suitable for use with non-homogeneous substances.

The "Journal of Microwave Power", Volume 14, 1979, No. 4, pages 363 to 365 discloses a strip-line sensor for measuring moisture by means of microwaves. A strip line provided on a substrate is enveloped by the substance to be measured which is penetrated by the stray field of the strip line. The moisture contained in the substance influences via the stray field the attenuation of the strip line which is connected to a measuring arrangement for attenuation measurement.

This arrangement, as is also the case for the coaxial aerial, has the disadvantage that the stray field is only present in the immediate vicinity of the strip line and that consequently only a small portion of the substance to be measured affects the attenuation of the strip line. This arrangement is therefore also not suitable for measurements on larger quantities of non-homogeneous substances. Moreover, attenuation measurements have the drawback that they are sensitive to interferences by standing waves, so that measurements made with the described arrangement become inaccurate.

In practice it is difficult to determine high moisture contents by means of microwaves as the highly aqueous substances on which the measurements are to be effected often consist of a small quantity of a material having a low permittivity, typically a value between approximately 2 and approximately 5, and a large quantity of water having a permittivity of approximately 80. The resultant permittivity of the aqueous substance then deviates only little from the permittivity of water, and changes in the water content affects the propagation properties of the substance, and consequently the measurements, to a very limited extent only.

SUMMARY OF THE INVENTION

It is an object of the invention to provide an arrangement for measuring the moisture content of an aqueous substance by employing microwaves, which even with high moisture contents, that is to say highly aqueous substances, renders a simple and accurate measurement which is not susceptible to interferences such as non-homogeneities of the substance and reflections and standing waves. According to the invention the transmit aerial radiates a substantially flat electro-magnetic wave into the substance, the receive aerial is provided by at least one measuring probe, and the phase of the wave transmitted through the substance is determined by the evaluation arrangement.

In a further embodiment of the invention the phase of the wave transmitted through the substance is compared in the evaluation arrangement with a reference.

In a still further embodiment of the invention at least two measuring probes are provided which are arranged with a fixed interspace with respect to each other in the direction of propagation of the wave, and the evaluation arrangement is of such a construction that it determines the difference between the phases of the waves received from the measuring probes.

In a further embodiment of the invention the transmitting arrangement radiates a frequency-modulated wave into the substance, only one measuring probe for receiving the wave transmitted through the substance is provided, and the evaluation arrangement determines the change in the phases of the received waves in dependence on its frequency.

The arrangement in accordance with the invention has the advantage that the wave is radiated into a large portion of the aqueous substance to be measured. The measurement performed with the arrangement in accordance with the invention is therefore not sensitive to non-homogeneities of the substance. Also the interfering influence of standing waves on the measuring accuracy is reduced in the arrangement in accordance with the invention as compared with prior art arrangements. The overall arrangement in accordance with the invention is of a simple structure, has the advantage that it continuously monitors the measuring value and is therefore suitable for use in moisture content measurements in automated processes.

In accordance with an advantageous embodiment of the invention all the measuring probes are provided by integrated microwaves circuits formed from at least two mating dielectric plates between which strip-shaped electric conductors are arranged and the outer faces of the outermost plates are coated at least partially with an electrically conducting layer.

In a further embodiment of the invention the integrated microwave circuit is arranged in the centre plane of a wave guide which is filled with a dielectric material.

In accordance with a still further embodiment of the invention the wave guide is in the form of a rectangular waveguide.

In yet another embodiment of the invention, the aerial and the measuring probe or measuring probes are combined in an integrated microwave circuit which has at least a first strip-shaped conductor acting as the aerial and signal supply means to the aerial and at least a second conductor acting as a measuring probe and signal discharge means for the measuring probe.

The last-mentioned embodiments of the aerial and the measuring probes are of a simple construction, can be produced within narrow mechanical tolerances and are rugged.

BRIEF DESCRIPTION OF THE DRAWING

Some embodiments of the invention will now be further described, by way of example, with reference to the accompanying drawing in which:

FIGS. 6, 7 and 8 show some embodiments of the invention,

DESCRIPTION OF THE PREFERRED EMBODIMENTS

Figure 1:
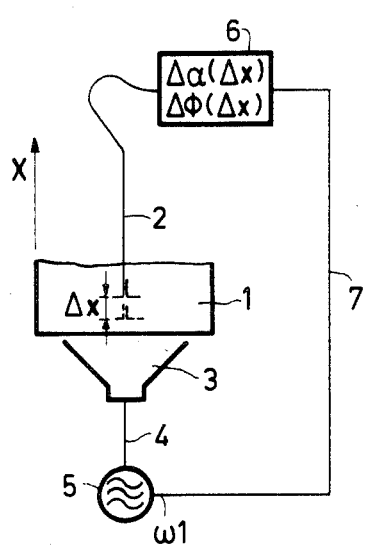
FIG. 1 is a circuit diagram for explaining the measuring principle according to the invention.

FIG. 1 shows the measuring principle on which the arrangement in accordance with the invention is based. A measuring probe 2, which is movable in the X-direction is inserted into the aqueous substance 1 to be measured. In line with the X-direction there is arranged before the measuring probe 2 an aerial 3, which is connected via a signal supply conductor 4 to a generator 5, which serves as a signal source. An evaluation arrangement 6 has a first input connected to the measuring probe 2 and a second input to the generator 5 via a reference line 7. The generator 5 produces a radio-frequency a.c. voltage. The aerial 3 radiates a substantially flat wave whose progagation direction coincides with the X-direction, into the aqueous substance 1. The evaluation arrangement 6 determines moisture content by comparing the wave received from the aerial 3 with a reference signal which is fed-in by the generator 5 over the reference conductor 7. The attenuation $\alpha$ and the phase $\phi$ of the received wave change with displacement of the measuring probe in the X-direction, and the evaluation arrangement measures the change $\Delta\alpha$ or $\Delta\phi$ respectively, with displacement of the probe through the distance $\Delta x$.

Figure 2:
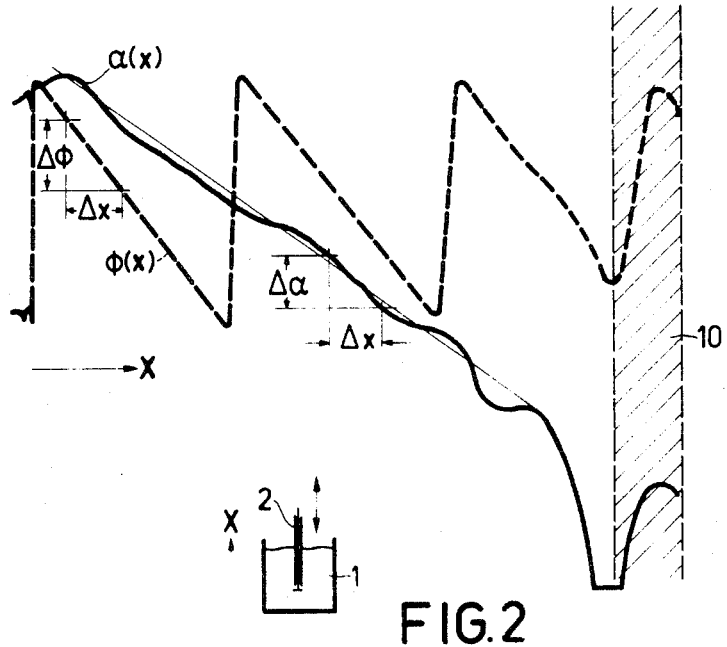
FIG. 2 shows diagrammatically the attenuation and the phase angle of the signal measured with the arrangement of FIG. 1.

FIG. 2 shows an example of measuring curves recorded by means of an arrangement as shown in the FIG. 1. The curves represent variation of the attenuation $\alpha$ and the phase $\phi$ for the displacement of the measuring probe 2 along the X-direction. A slurry of milk powder in water was used as the aqueous substance 1. The phase $\phi(x)$ has a more uniform variation with displacement of the measuring probe 3 than the attenuation $\alpha$ and is therefore preferably used for measuring the moisture content. As a measure of the moisture content, the phase change versus the displacement distance $\Delta\phi/\Delta x$ is used, as it is in a direct relationship with the moisture content of the substance via the propagation rate of the wave in the aqeous substance and the permittivity thereof. When the measuring probe 2 is in the immediate vicinity of the surface of the measured substance 1 then the curves $\alpha$ and $\phi$ evidence considerable non-uniformities, which are caused by surface effects, such as for example reflections, and which are illustrated in FIG. 2 by means of the hatched area 10. This area must not be used for the moisture content measurement.

Figure 3:
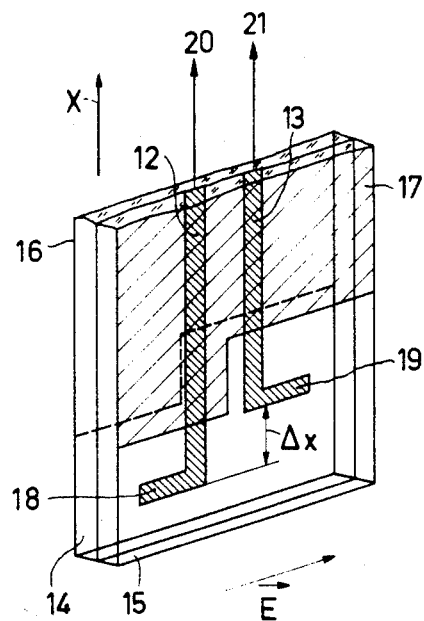
FIG. 3 shows an embodiment of the measuring probes according to the invention.

Because a moveable measuring probe is difficult to handle, the arrangement in accordance with the invention preferably employs fixed measuring probes. FIG. 3 shows an embodiment of an arrangement in accordance with the invention having two measuring probes which are incorporated in an integrated microwave circuit. Two strip-shaped conductors 12 and 13, which extend in parallel with the propagation direction of the wave, that is to say in parallel with the X-direction, are provided between two dielectric plates 14 and 15. The ends 18 and 19 of the strip conductors 12 and 13 are arranged perpendicularly to the X-direction and form the measuring probes, which are separated by a distance $\Delta x$ in the X-direction and are arranged in the form of a dipole in parallel with the field lines of the electric field E of the wave which is transmitted through the aqueous substance. The outer faces of the dielectric plates 14 and 15 are coated with conductive layers 16 and 17, which form a shield for the strip-conductors 12 and 13. Only the folded ends 18 and 19 of the strip conductors 12 and 13, which then serve as the measuring probes, extend from the shielding. The measuring probes 18 and 19 have corresponding dimensions and consequently largely corresponding electric properties. The distance $\Delta x$ is less than the wavelength in the aqueous substance 1 and particularly less than the wavelength in pure water. The evaluation arrangement is connected to terminals 20 and 21 of the strip conductors 12 and 13, and measures the moisture content of the substance 1 by measuring the phase difference between the voltages received by the measuring probes 18 and 19 and applied to the terminals 20 and 21. When the described arrangement of the measuring probes is employed, the aerial 3 of the transmitting arrangement is a module which is spatially separated from the measuring probes.

Figure 4A:
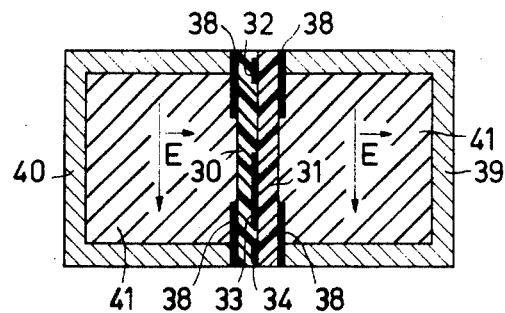
FIGS. 4a and 4b show an arrangement in which the aerial and the microprobes are combined in one integrated microwave circuit according to the invention.
Figure 4B:
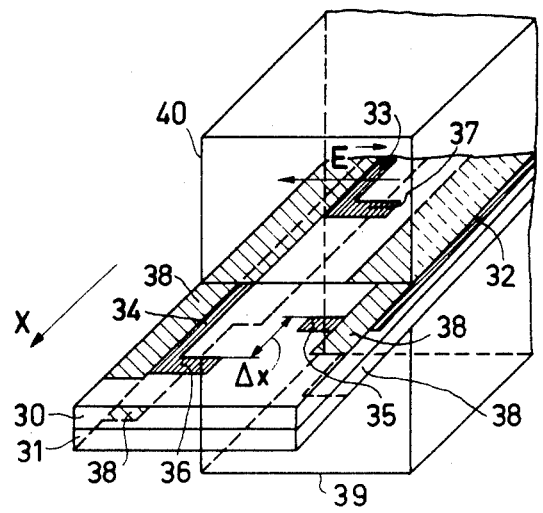

FIGS. 4a and 4b a further embodiment in which the aerial of the transmitting arrangement and the measuring probes are combined in one module. FIG. 4a shows a crosssectional view through the combined arrangement of the aerial and measuring probes and FIG. 4b shows a perspective view. Several strip conductors 32, 33 and 34, which extend in parallel with the X-direction which corresponds to the propagation direction of the wave are arranged between two dielectric plates 30 and 31, whose surfaces are next to each other. The ends of the conductors 32 and 34 are folded perpendicularly to the X-axis and form the measuring probes 35 and 36, as has been described already with reference to FIG. 3. The conductor 33 is also folded perpendicularly to the x-axis; the folded portion 37 provides the aerial of the transmitting arrangement. The aerial 37 and the measuring probes 35 and 36 are arranged in parallel to the direction of the field lines of the electric field E. In the X-direction the measuring probes 35 and 36 are spaced by $\Delta x$. The outermost surfaces of the dielectric plates 30 and 31 are partially coated with conductive layers, which form the shield for the strip-conductors 32, 33 and 34. The aerial 37 and the measuring probes 35 and 36 extend from under this shield. The dielectric plates 30 and 31 are arranged between the halves 39 and 40 of a rectangular wave guide which is cut open through its longitudinal centre plane and is filled with a dielectric 41. The portion of the dielectric plates 30 and 31 in which the measuring probes 35 and 36 are arranged extends from the end of the rectangular waveguide 39, 40. The aerial 37 produces in the waveguide the $H_{10}$-wave which is radiated from the end of the waveguide as a wave which is substantially flat in the region of the measuring probes 35 and 36 and is received by the measuring probes 35 and 36. To effect a moisture measurement, the overall arrangement is inserted into the substance to be measured.

Figure 5:
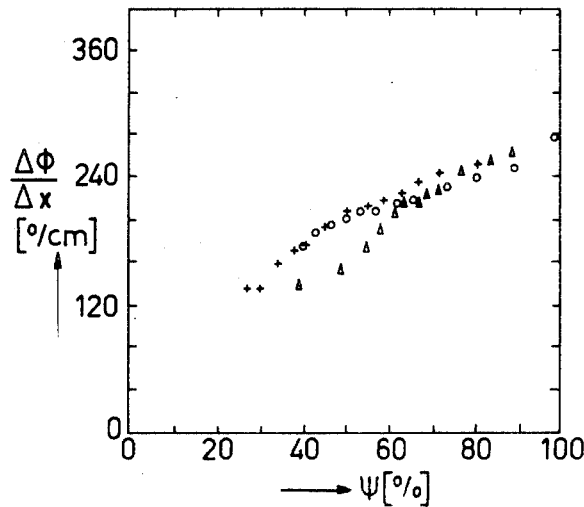
FIG. 5 shows results of some moisture content measurement effected by means of an arrangement in accordance with the invention.

FIG. 5 shows some measuring results. The phase change versus distance $\Delta\phi/\Delta x$ measured in an arrangement in accordance with the invention is plotted in angular degrees/cm for the relative moisture $\phi$ of the substance measured in %.

FIG. 6 shows a first embodiment of an arrangement in accordance with the invention for moisture measurement. It is shown that the arrangement uses, for example the measuring probes described in FIGS. 3 and 4a/4b. Two measuring probes 2 and 2', which are arranged in such a way that they are spaced by $\Delta x$ in the X-direction and are connected to the inputs of two amplifier stages 50 and 51 are immersed in the aqueous substance to be measured. As is shown in FIG. 1, the aerial 3 radiates a substantially flat wave into the aqueous substance 1. The a.c. voltages received by the measuring probes 2 and 2' are amplified in the amplifier stages 50 and 51 and applied to the mixer 52, which is connected to the outputs 53 and 54 of the amplifier stages 50 and 51 and determines the phase difference between the two a.c. voltages.

FIG. 7 shows a further embodiment of a measuring arrangement in accordance with the invention. A single side-band generator 60 is connected to a carrier frequency generator 61, which produces a radio-frequency a.c. voltage having an angular frequency $\omega_1$ and an intermediate frequency generator 62, which produces an a.c. voltage having the angular frequency $\Delta\omega$. From the two voltages the single-side band generator 60 forms a single-side band modulated signal, which is applied to the aerial 3 via the conductor 4. The aerial 3, the measuring probes 2 and 2' and the aqueous substance 1 are arranged in the same way as in FIG. 6. The measuring probes 2 and 2' are each directly connected to the signal inputs of respective mixers 64 and 65, while the carrier frequency generator 61 is connected to the local oscillator inputs of the two mixers 64 and 65 via a 3 dB power divider 63. In this way the signals received from the measuring probes are converted to the intermediate frequency. The mixers 64 and 65 are connected to a phase discriminator 66, which determines the phase difference $\Delta\phi$ of the a.c. voltages applied to the intermediate-frequency outputs of the mixers 64 and 65.

FIG. 8 shows a third embodiment of the arrangement in accordance with the invention, comprising only one measuring probe 2. In this arrangement the transmitting arrangement 5 is in the form of a voltage-controlled oscillator 70, which is connected to a voltage generator 71. The oscillator 70 produces an a.c. voltage whose angular frequency is modulated by generator 71 around an angular frequency $\omega_1$ by applying a voltage of predetermined waveform representing a frequency change $\Delta\omega$. The measuring probe 2 is connected to a phase discriminator 75, which is formed in the manner shown schematically in the drawing by a mixer 77 and a delay line 76. In the conductor from the measuring probe 2 to the phase discriminator 75 a frequency converter stage 72, formed by an oscillator 73 and a mixer 74 may optionally be incorporated. The wave radiated by the aerial 3 into the substance 1 in the manner described in the foregoing is received by the measuring probe 2. The a.c. voltage thus produced at the measuring probe 2 is converted to a base-band-frequency by the frequency converter stage 72, if applicable. The phase of the received wave is in a proper approximation proportional to its frequency and to the square of the real part of the complex permittivity of the substance 1. The subsequent phase discriminator 75 determines the deviation of the phase in accordance with the angular frequency, which, with non-dispersive or only weakly dispersive substances, is proportional to the square of the real portion of the complex permittivity of the substance. Consequently, the signal produced at the output of the phase discriminator 75 furnishes a direct measure for the moisture content of the substance 1.

What is claimed is:

1. An apparatus for measuring the moisture content of an aqueous substance, comprising:
    (a) transmitting means arranged for radiating a substantially flat AC electromagnetic wave into the aqueous substance;
    (b) receiving means including at least one probe disposed in the aqueous substance for sensing the electromagnetic wave at first and second positions separated by a predetermined distance in the direction of propagation of the wave through the aqueous substance;
    (c) evaluation means electrically-coupled to the receiving means for measuring the change in phase of the electromagnetic wave across said predetermined distance, said change in phase representing the moisture content of the aqueous substance.

2. An apparatus as in claim 1 where said receiving means comprises a moveable probe which is adapted for movement between said first and second positions.

3. An apparatus as in claim 1 where said receiving means comprises first and second probes located at said first and second positions.

4. An apparatus for measuring the moisture content of an aqueous substance, comprising:
    (a) transmitting means arranged for radiating a substantially flat, frequency-modulated electromagnetic wave into the aqueous substance;
    (b) receiving means including a probe disposed in the aqueous substance for sensing the electromagnetic wave; and
    (c) evaluation means electrically-coupled to the receiving means for measuring the change in phase of the electromagnetic wave for a predetermined change in its frequency, said change in phase representing the moisture content of the aqueous substance.

5. An apparatus as in claim 1, 2, 3 or 4 where the receiving means comprises:
    (a) first and second dielectric plates having respective inner faces adjacent to each other;
    (b) at least one strip-type conductor disposed between the inner surfaces of the dielectric plates, an end of said conductor forming said probe; and
    (c) first and second conductive layers disposed on respective outer faces of the first and second dielectric plates, said conductive layers leaving uncovered the end of the strip-type conductor forming the probe.

6. An apparatus as in claim 5 where the dielectric plates extend from the center of a waveguide filled with dielectric material, said end of the strip-type conductor being situated outside of said waveguide.

7. An apparatus as in claim 6 where said waveguide is rectangular.

8. An apparatus as in claim 6 where the transmitting means comprises a strip-type conductor disposed between the faces of the dielectric plates and having an end forming a transmitting aerial for transmitting the electromagnetic wave toward the probe.

* * * * *